US006060236A

United States Patent [19]
Clements et al.

[11] Patent Number: 6,060,236
[45] Date of Patent: *May 9, 2000

[54] BORNA DISEASE VIRUS-SPECIFIC DNA AND PROTEINS

[75] Inventors: Janice E. Clements, Columbia; Opendra Narayan, Timonium, both of Md.; Susan Vandewoude, Loveland, Colo.; Juergen A. Richt, Moensheim, Germany

[73] Assignee: The Johns Hopkins University School of Medicine, Baltimore, Md.

[ * ] Notice: This patent is subject to a terminal disclaimer.

[21] Appl. No.: 09/222,227

[22] Filed: Dec. 29, 1998

Related U.S. Application Data

[62] Division of application No. 08/455,976, May 31, 1995, Pat. No. 5,854,417, which is a division of application No. 08/387,903, Mar. 30, 1995, Pat. No. 5,654,104, which is a continuation of application No. 07/618,288, Nov. 28, 1990, abandoned.

[51] Int. Cl.[7] .................................. C12Q 1/70
[52] U.S. Cl. ................... 435/5; 435/6; 435/7.1; 530/350; 530/826; 935/2; 935/3; 935/6; 935/12; 935/76; 935/77
[58] Field of Search .................... 435/5, 7.1, 6; 530/350, 530/826; 935/2, 3, 6, 12, 76, 77

[56] References Cited

PUBLICATIONS

Koprowski H., "Detection of Serum Antibodies to Borna Disease Visur in Patients with Psychiatric Disorders," *Science*, vol. 228, pp. 755–756.

Haas et al., "Purification and Properties of an Intranuclear Virus–Specific Antigen from Tissue Infected with Borna Disease Virus," *The Journal of General Virology*, (1986), 67, pp. 235–241.

Schadler et al., "Isolation and Characterization of a 14500 Molecular Weight Protein from Brains and Tissue Cultures Persistently Infected with Borna Disease Virus," *The Journal of General Virology*, (1985), 66, pp. 2479–2484.

Young et al., "Genes for the major protein antigens of the leprosy parasite Mycobacterium leprae," *Nature*, vol. 316, Aug. 1, 1985, pp. 450–452.

Lipkin et al., "Isolation and characterization of Borna disease agent cDNA clones", *Proc. Natl. Acad. Sci. USA*, vol. 87, pp. 4184–4188, Jun. 1990.

Helfman et al., "Use of Antibodies to Screen cDNA Expression Libraries Prepared in Plasmid Vectors", *Methods in Enzymology*, vol. 152, pp. 451–457.

Young et al., "Efficient isolation of genes by using antibody probes", *Proc. Natl. Acad. Sci. USA*, vol. 80, pp. 1194–1198, Mar. 1983.

*Primary Examiner*—Jeffrey Stucker
*Attorney, Agent, or Firm*—Fish & Richardson P.C.

[57] ABSTRACT

Borna disease virus (BDV) causes a rare neurological disease in horses and sheep. A subtractive cDNA expression library was constructed with poly A-selected RNA from a BDV infected MDCK cell line. A clone (B8) was isolated that specifically hybridizes to RNA isolated from BDV-infected brain tissue and BDV-infected cell lines. This clone hybridizes to four BDV-specific positive strand RNAs and one negative strand RNA in BDV-infected rat brain. Nucleotide sequence analysis of the clone suggests that it represents a full length mRNA which contains several open reading frames. The Borna Disease Virus DNA sequences as well as proteins encoded by the BDV DNA sequences are provided.

7 Claims, 4 Drawing Sheets

BORNA DISEASE VIRUS-SPECIFIC DNA AND PROTEINS

This is a divisional of U.S. application Ser. No. 08/455,976, filed May 31, 1995, now issued as U.S. Pat. No. 5,854,417 on Dec. 29, 1998, which is a divisional of U.S. Appl. Ser. No. 08/387,903, filed Mar. 30, 1995, now U.S. Pat. No. 5,654,104, issued Aug. 5, 1997, which is a continuation of U.S. patent application Ser. No. 07/618,288, filed Nov. 28, 1990, now abandoned.

This invention was made using U.S. government funds awarded by the National Institutes of Health. Therefore the government retains certain rights in the invention.

BACKGROUND OF THE INVENTION

Borna disease is an infectious neurological disease that occurs sporadically in horses and sheep in Central Europe (Ludwig, Prog. Med. Virol. 35:107 (1988)). Brain homogenates from infected animals can be used to infect a large number of animal species from rodents to non-human primates (Carbone, Virol. 61:3431 (1987); Narayan, Science 220:1401 (1983); Sprankel, Med. Microbiol. Innumol. 165:1 (1978)). Studies in rats have shown that the agent is highly neurovirulent and invades the brain from peripheral sites by axonal transport (Carbone, supra). It replicates in specific groups of neurons in the cerebral cortex and causes biphasic behavioral disease characterized by aggression and hyperactivity during the acute phase of infection and apathy and eating disorders during the chronic stage (Narayan, supra). In tree shrews (*Turpaia glis*), infection is associated with disruption in social interactions (Sprankel, supra). In addition, recent studies demonstrate the presence of anti-Borna Disease Virus (BDV) antibodies in humans with psychiatric illnesses which include personality disorders and schizophrenia (Rott, Science, 228:755 (1985); Amsterdam, Arch. Gen. Psychiatry, 42:1093 (1985)).

The BDV virus replicates in cell cultures and rat brain with the synthesis or novel 38/39, 24 and 14 kD proteins (Haas, J. Gen. Virol. 67:235 (1986)). However, the virus has not been classified since neither a particle nor a specific nucleic acid has been identified in infectious material.

SUMMARY OF THE INVENTION

It is an object of the invention to provide a DNA molecule which is specific for the Borna Disease Virus.

It is yet another object of the invention to provide Borna Disease Virus proteins which are substantially pure.

It is an object of the invention to provide means to isolate Borna Disease Virus-related human viruses.

It is still another object of the invention to provide kits and methods for diagnosing Borna Disease Virus infections and Borna Disease Virus-related human virus infections in humans.

These and other objects of the invention are provided by one or more of the embodiments which are described below. In one embodiment, a DNA molecule is provided which is complementary to the genome of BDV.

In another embodiment a DNA molecule is provided which is complementary to BDV-encoded messenger RNA.

In still another embodiment of the invention a duplex DNA molecule is provided which comprises a DNA molecule which is complementary to the genome of Borna Disease Virus or a DNA molecule which is complementary to a Borna Disease Virus-encoded messenger RNA.

In yet another embodiment of the invention a preparation of Borna Disease Virus-encoded protein is provided, which preparation is substantially free of mammalian proteins.

In another embodiment of the invention a DNA molecule is provided which is complementary to a BDV-related, human virus-encoded messenger RNA.

In still another embodiment of the invention a DNA molecule is provided which has the same polarity as a BDV-related, human virus-encoded messenger RNA, said molecule bybridizing to a DNA molecule which is complementary to a Borna Disease Virus-encoded messenger RNA.

In yet another embodiment of the invention a duplex DNA molecule is provided which comprises a first DNA molecule which is complementary to a BDV-related, human virus-encoded messenger RNA or a second DNA molecule having the same polarity as a BDV-related, human virus-encoded messenger RNA, said second DNA molecule hybridizing to a DNA molecule which is complementary to a Borna Disease Virus-encoded messenger RNA.

In another embodiment of the invention a method is provided for determining a Borna Disease Virus infection in animals or a Borna Disease Virus-related human virus infection in humans, comprising the steps of:

providing a serum sample of an animal or human to be tested;

contacting the serum sample with a preparation of Borna Disease Virus-encoded protein substantially free of mammalian proteins, under conditions where antibody-antigen complexes form and are stable;

determining the presence of antibody-antigen complexes which contain said Borna Disease Virus-encoded protein, the presence of antibody-antigen complexes which contain said Borna Disease Virus-encoded protein indicating a Borna Disease Virus infection or a Borna Disease Virus-related human virus infection.

In yet another embodiment of the invention a kit is provided for determining a Borna Disease Virus infection in animals or a Borna Disease Virus-related human virus infection in humans, comprising:

a solid support; and a preparation of Borna Disease Virus-encoded protein substantially free of mammalian proteins, said Borna Disease Virus-encoded proteins bound to said solid support.

In another embodiment of the invention a method is provided for determining a Borna Disease Virus infection in animals or a Borna Disease Virus-related human virus infection in humans, comprising the steps of:

providing a sample of cells from an animal or human to be tested;

extracting RNA from said cells;

contacting said RNA with a DNA probe, said probe comprising a DNA molecule which is complementary to a Borna Disease Virus-encoded messenger RNA;

determining the presence of hybrid molecules comprising said probe, the presence of said hybrid molecules indicating a Borna Disease Virus infection or a Borna Disease Virus-related human virus infection.

In still another embodiment of the invention a method is provided for determining a Borna Disease Virus infection in animals or a Borna Disease Virus-related human virus infection in humans, comprising the steps of:

providing a sample of cells from an animal or human to be tested;

permeabilizing said cells;

contacting said permeabilized cells with a DNA probe, said probe comprising a DNA molecule which is complementary to a Borna Disease Virus-encoded messenger RNA;

determining the presence of hybrid molecules comprising said probe, the presence of said hybrid molecules indicating a Borna Disease Virus infection or a Borna Disease Virus-related human virus infection.

In another embodiment of the invention a method is provided for determining a Borna Disease Virus-related human virus infection in humans, comprising the steps of:

providing a sample of cells from a human to be tested;

extracting RNA from said cells;

contacting said RNA with a DNA probe, said probe comprising a DNA molecule which is complementary to a Borna Disease Virus-related human virus-encoded messenger RNA;

determining the presence of hybrid molecules comprising said probe, the presence of said hybrid molecules indicating a Borna Disease Virus-related human virus infection.

In still another embodiment of the invention a method is provided for determining a Borna Disease Virus-related human virus infection in humans, comprising the steps of:

providing a sample of cells from a human to be tested;

permeabilizing said cells;

contacting said permeabilized cells with a DNA probe, said probe comprising a DNA molecule which is complementary to a Borna Disease Virus-related human virus-encoded messenger RNA;

determining the presence of hybrid molecules comprising said probe, the presence of said hybrid molecules indicating a Borna Disease Virus-related human virus infection. These and other embodiments of the invention provide the art with nucleic acids and proteins which can be used to diagnose BDV and BDV-like infections of humans and other mammals. In addition, it provides the tools for isolation and identification of the viral agents which cause these neurological diseases.

Northern blot analysis of RNA (10 ug/lane) from: (a) uninfected MDCK (Madin Darby canine kidney) cells; (b) BDV-infected MDCK cells; (c) uninfected rat brain; (d) BDV-infected rat brain; (e) BDV-infected MDCK cells; and (f) BDV-infected rat brain. The northern blot was hybridized with a nick translated probe made from DNA from the B8 clone.

FIG. 2 shows the determination of polarity of BDV-specific RNAs A. Negative strand $^{32}$P-UTP-labeled RNA transcripts of clone B8 hybridized to Northern blots containing: (a) 7.5 ug of RNA from uninfected rat brain; (b) 7.5 ug of RNA from BDV-infected rat brain; and (c) 2.0 ug of poly A selected RNA from BDV-infected rat brain. B. Positive strand $^{32}$P-UTP-labeled RNA transcripts of clone P4 hybridized to northern blots containing: (a) 7.5 ug of RNA from uninfected rat brain; and (b) 7.5 ug of RNA from BDV-infected rat brain. RNA from BDV-infected rat brain was heated at 90° C. for 2 min and chromatographed on oligo-dt cellulose and RNA was used in northern blots: (c) 5 ug of total RNA from BDV-infected rat brain; (d) 3 ug RNA from oligo-dt column wash; and (e) 3 ug of Poly A-containing RNA.

Figure 3A:
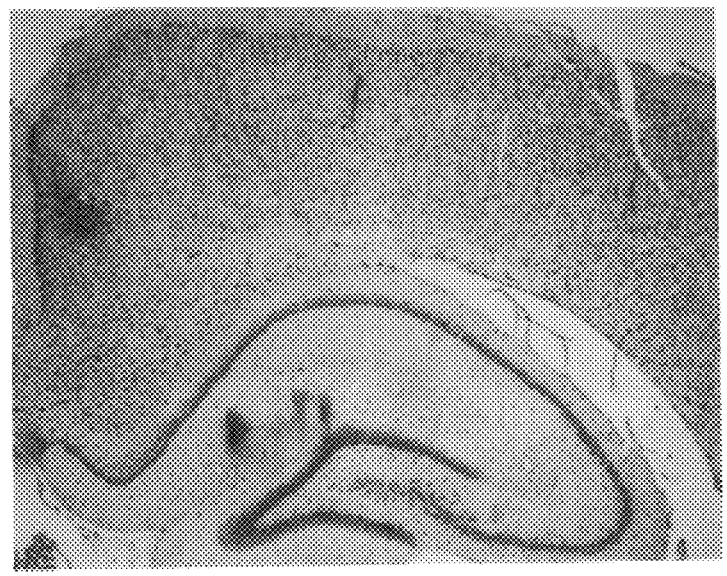

FIG. 3 shows the results of in situ hybridization of BDV infected rat brain with the B8 clone. Brains from (a) uninfected and (b) BDV-infected rats were fixed in formaldehyde, dehydrated and paraffin-embedded.

Figure 4:
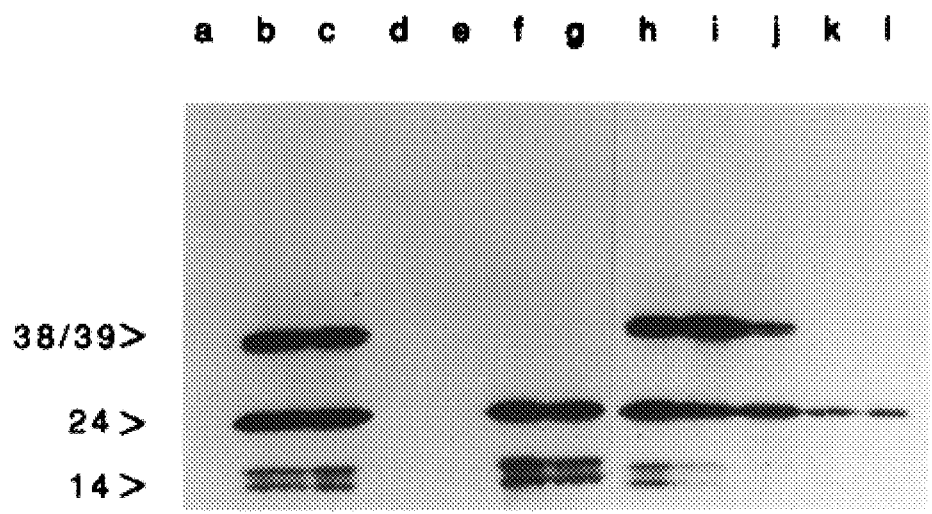

FIG. 4 shows the identification of BDV-specific proteins encoded by the B8 clone. Poly-A selected RNA from uninfected rat brain (lanes a and b) and BDV-infected rat brain (lanes c, d, l, m and n) were translated in vitro and immunoprecipitated with polyclonal anti-BDV sera from rat (lanes a, c and l), rabbit (lanes b and d), or monoclonal antibodies to the 38/39 kD protein (lane m) and the 24 kD protein (lane n). In vitro transcription with T7 polymerase synthesized the negative stranded RNA from the B8 clone and positive stranded RNA from the P4 clone. RNA transcribed in vitro from clone B8 (lanes e and f) and clone P4 (lanes g, h, o and p) were translated in vitro and immunoprecipitated with polyclonal anti-BDV sera from rat (lanes e and g) rabbit (lanes f and h) or monoclonal antibodies to the 38/39 kD protein (lane o) and 24 kD protein (lane p). Controls (lanes i, j , q and r) are in vitro translation reactions without RNA which were immunoprecipitated with polyclonal anti-BDV sera from rats (lane i), rabbit (lane j) 38/39 kD monoclonal antibodies (lane q) and 24 kD monoclonal antibodies (lane r). Molecular weight markers ($^{14}$C-labelled) in lane k contain from top to bottom 200, 92.5, 69, 46, 30, 21.5, and 14.3 kD proteins.

Figure 5:
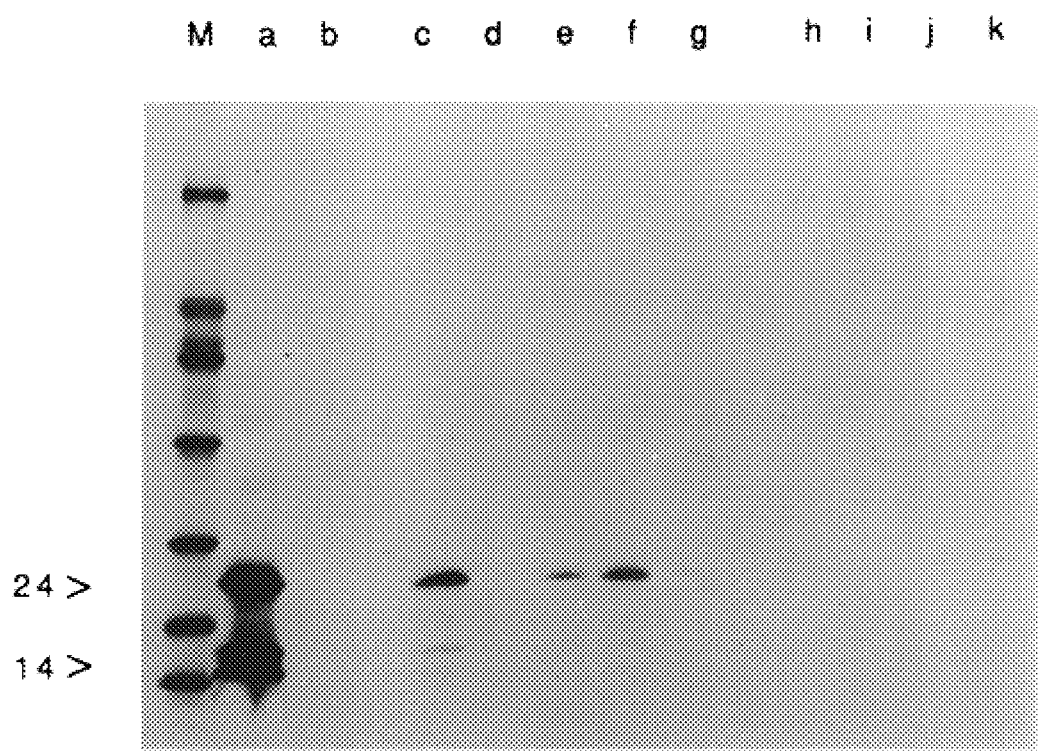

FIG. 5 shows analyses of antibodies in human serum by immunoprecipitation of the BDV-specific proteins translated from the B8 clone. The lanes contain $1\times10^5$ cpm of $^{35}$S-methionine-labelled proteins immunoprecipitated with the following sera: BDV infected rat (a); normal rat (b); human anti-BDV-p24 (c); human anti-BDV-p38/39(d); patient 112 (e); patient 114 (f); patient 115 (g), and normal human sera in lanes (h–k). Lane M contains molecular weight markers ($^{14}$C-labelled) from top to bottom 200, 92.5, 69, 46, 30, 21.5 and 14.3 kD proteins.

DETAILED DESCRIPTION OF THE INVENTION

Isolation of BDV-specific cDNA

Figure 1:
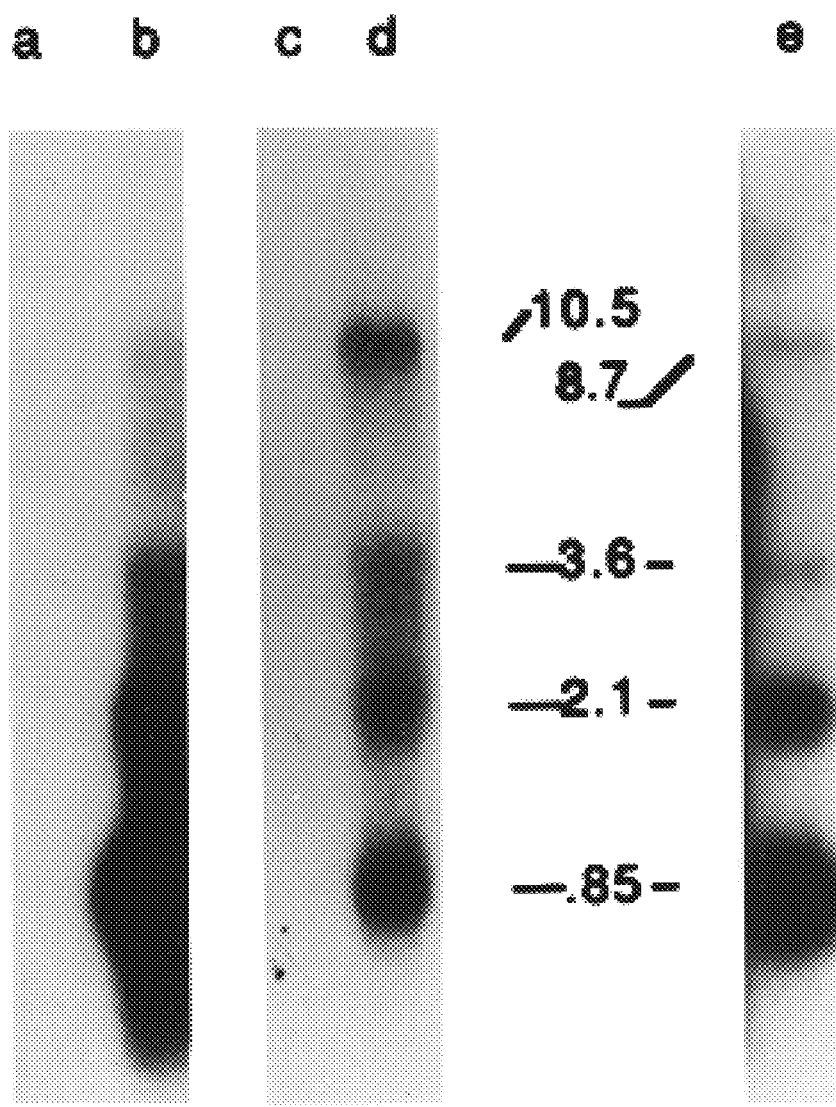
FIG. 1 shows specific hybridization of a cDNA clone to RNA isolated from BDV-infected cells and rat brain.

To identify and clone a BDV-specific nucleic acid a subtractive cDNA library was constructed from the mRNA isolated from uninfected and BDV-infected MDCK cell lines. Two rounds of selection were performed to enrich the cDNA library for BDV-specific cDNAs. The vector used for cloning contained a polylinker in the lac z gene into which inserts were cloned; this allowed bacterial expression of a fusion protein. Colonies were grown in the presence of IPTG to induce expression from the lac z promoter and were screened using monoclonal antibodies specific for the BDV 38/39 kD protein (Haas, J. Gen. Virol. 67:235 (1986)). Nine antibody positive clones were identified. The DNA from these clones was nick translated and hybridized to Northern blots containing RNA from uninfected and BDV-infected rat brain. One clone specifically hybridized to RNA from infected rat brain and showed no hybridization to RNA from uninfected rat brain (FIG. 1). This clone, called B8, contained a 700 bp BDV-specific insert which is an apparently full length mRNA. The B8 clone hybridized to four RNAs of 10.5 or 8.7, 3.6, 2.1 and 0.85 kb in BDV-infected rat brain and cell cultures (FIG. 1). These four RNAs are enriched by poly A selection and are apparently positive strand mRNAs. Further, it was reproducibly found that the largest RNA species in rat brain was 10.5 kb in contrast to 8.7 kb in BDV-infected cell cultures (FIG. 1, lanes e and f). This difference may reflect the presence of a defective genome in the persistently infected cell cultures.

Methods: Standard molecular techniques were used (Maniatis, *Molecular Cloning*, Cold Spring Harbor Laboratory, (1990)). The cDNA libraries were constructed using poly A selected RNA from uninfected and infected MDCK cells using reagents and methods in the Invitrogen Librarian kit. The modified Gubler Hoffman technique (Gubler, Gene 25:263 (1983);Duguid, P.N.A.S. 85:5738 (1988); Sive, Nuc. Acids Res. 16:10937 (1988); Dower, Nuc. Acids Res 16:6127 (1988)) was used for the synthesis of the cDNA; cDNAs were not size selected. Colonies of the subtracted library were grown in the presence of IPTG and lifted onto nylon membranes. The microwave method was used to fix proteins to the filters (Invitrogen). A mix of monoclonal antibodies to the 38/39 kD Borna-specific antigen was used to detect clones expressing Borna-specific proteins. The DNA from nine positive clones was nick translated and used as probes on northern blots of RNA from BDV-infected and uninfected rat brain. RNA was prepared using standard techniques (Chomczynski, Analytical Biochem. 162:156 (1987); Puissant, Biotechniques 8:148 (1990)). Samples were run on a formaldehyde denaturing gel and transferred to nylon membranes (Thomas, P.N.A.S. 77:5201 (1980)). Sizes were determined by comparison with a radiolabeled RNA ladder (BRL). Specific hybridization to the RNA from infected brain was detected in one of the nine clones (clone B8).

Polarity of RNA Species

Figure 2A:
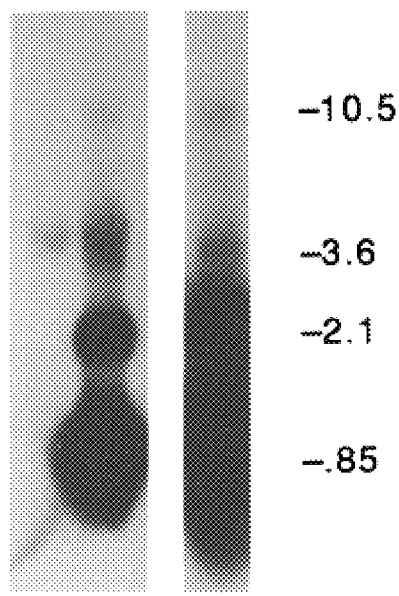
Figure 2B:
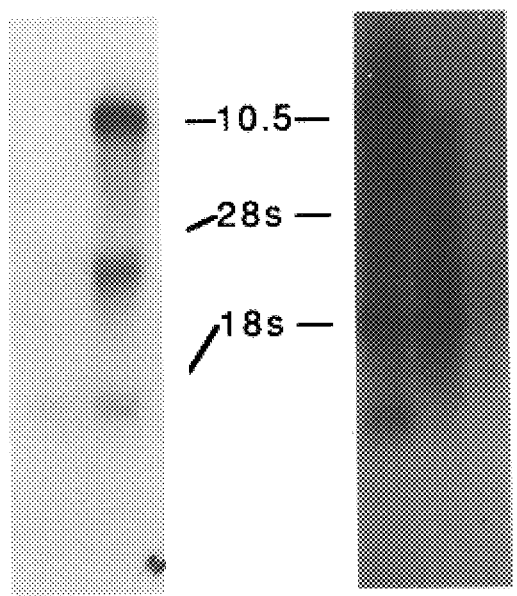

To determine the polarity of the RNA species in the BDV-infected cell cultures and tissues, strand specific RNA probes were made from the B8 clone. The polarity of the B8 clone was determined by sequence analysis. The sequence of the B8 clone is provided in SEQ ID NO: 1. At one end of the clone a stretch of As were found and at the other end a number of ATGs were found preceding open reading frames. The negative strand probe showed a similar hybridization pattern to the nick translated B8 clone and identified four BDV-specific transcripts (10.5, 3.6, 2.1 and 0.85 kb) in BDV infected rat brain RNA (FIG. 2A). This negative strand probe also hybridized to these same sized RNAs from poly A selected RNA (FIG. 2A). The presence of apparently subgenomic mRNAs (3.6, 2.1 and 0.85 kb) all of which hybridize with the negative strand of the B8 clone, suggest that these mRNAs contain common sequences. In contrast, the positive strand probe hybridized only to a 10.5 kb RNA in BDV-infected rat brain (FIG. 2B).

Methods: Clone P4 was constructed by subcloning the entire B8 cDNA insert into the PGEM3 vector (Promega). Sequence analysis revealed that T7 polymerase would direct transcription of the positive strand of the P4 cDNA clone and the negative strand of the B8 cDNA clone. After linearizing the plasmids with restriction enzyme digestion, T7 polymerase was used to direct RNA synthesis in vitro for both constructs, $^{32}$P-UTP was used in the reaction to label the transcripts. RNA was isolated from tissues and cells and Northern blots were prepared as described in FIG. 1. Polyadenylated RNA was selected by chromatography on oligo-dt cellulose. Hybridization to Northern blots was done using standard conditions. Stringent washes were performed using 0.1×SSC at 65° C. for 2 hours.

No BDV Sequences in Genomic DNA

In order to eliminate the possibility that the BDV agent is a DNA virus or that the B8 clone represents a cellular gene whose expression was increased in BDV-infected cells, Southern hybridization was done with DNA isolated from uninfected and BDV-infected rat brain and MDCK cells. A single copy gene equivalent of the B8 clone was run in parallel and was detected under the hybridization conditions used (Southern, J. Mol. Biol. 98:503 (1975); Hogan, in *Manipulating the Mouse Embryo*, Cold Spring Harbor Laboratory, 180 (1986)). Using the nick translated B8 clone as a probe (Rigby, J. MOl. Biol. 113:237 (1977)), no hybridization was detected on Southern blots containing 10 ug of DNA from either the BDV-infected or uninfected tissues and cells (data not shown).

In Situ Hybridization

Figure 3B:

In order to further demonstrate the specificity of the B8 clone for the BDV agent, the clone was labelled with $^{35}$S-ATP by nick translation and in situ hybridization was done on sections of uninfected and BDV-infected rat brain. The B8 clone hybridized only to RNA in infected brain. Hybridization was localized to neurons in the cerebral cortex, thalamus, the dentate gyrus and the CA4 and CA3 regions of the pyramidal gyrus of the hippocampus (FIG. 3b). This pattern of hybridization is remarkably similar to the localization of BDV antigen established by classical histopathological and immunocytochemical techniques (Gosztonyi, Neuropsychiatry Clinics, 3:107 (1984)).

Methods: Six uM tissue sections were deparaffinized and treated as previously described (Zink, J. Pathol. 136:1250 (1990)). The DNA from the B8 clone was radiolabelled by nick translation using [$^{35}$S]dATP and [$^{35}$S]dCTP (Rigby, supra; Zink supra,) as previously described (Thomas, supra). Specific activities of the radiolabelled DNA probes vere greater than $7 \times 10^8$ cpm/ug. Radiolabelled DNA at a concentration of 0.2 ug/ml was hybridized to the sections as previously described (Zink, supra). The slides were exposed for 2 to 5 days, developed and examined by light microscopy; the presence of viral RNA was indicated by silver grains over cells. Sections of uninfected and BDV-infected rat brain hybridized with an irrelevant probe were used as negative controls for every hybridization reaction. To determine whether the B8 clone encoded BDV-specific proteins, the clone was transcribed in vitro in both orientations. The RNAs were translated in a rabbit reticulocyte lysate with $^{35}$S-methionine and the proteins analyzed by immunoprecipitation with polyclonal and monoclonal antibodies to BDV (FIG. 4). In parallel, poly A selected RNA from BDV-infected rat brain was translated and analyzed by immunoprecipitation with the same BDV-specific antibodies (FIG. 4). RNA corresponding to the positive strand of the B8 clone directed the synthesis of four proteins (24, 15.5, 14.5 and 13 kD) which were recognized by BDV-specific polyclonal antibodies. In addition, some monoclonal antibodies to both the 38/39 kD and 24 kD BDV proteins immunoprecipitated the same bands (kindly provided by L. Stitz). The mRNA from rat brain directed the synthesis of the 38/39, 24, 15.5 14.5 and 13 kD proteins which were immunoprecipitated by the BDV-specific polyclonal and monoclonal antibodies. These data provide further evidence that the B8 clone is a BDV-specific nucleic acid and encodes BDV-specific proteins.

Methods: Rat brain RNA was isolated and poly A selected (Maniatis, supra. Chomczynski, supra, and Puissant, supra). 0.5 ug of poly A selected RNA was translated in vitro using Staphylococcal-nuclease treated rabbit reticulocyte lysate (Promega) and $^{35}$S-methionine as a label. In vitro transcription of clones B8 and P4 was carried out with 1 ug of linearized DNA template in a standard reaction with T4 polymerase and m'G(5') pppG (cap analog) (Stratagene). 0.1 ug of this RNA was used in the in vitro translation system described above. Immunoprecipitation (using $1 \times 10^5$ cpm/sample) was carried out at 37° C. for one hour (polyclonal sera) or 4 hours (monoclonal sera) followed by addition of Protein A Sepharose beads and overnight incubation at 4° C.(14). Samples were run on 5 to 20% gradient SDS polyacrylamide gels and fluorography was performed (Entensify, New England Nuclear). Gels were dried and exposed at −70° C.

Immunoprecipitation of BDV Proteins by Human Sera

Antibodies to BDV have previously been identified in the serum of psychiatric patients by indirect immunofluorescence (Rott, supra; and Amsterdam, supra). To examine whether anti-BDV antibodies in human sera would recognize the virus-specific proteins encoded by the B8 clone, sera from normal controls (Rott, supra) and psychiatric patients (Rott, supra) with behavioral disorders from areas in Germany endemic for BDV were tested. The serum from two of the patients had previously been shown to have antibodies to BDV infected MDCK cells by indirect immunofluorescence. One serum recognized the BDV 24 kD and one the 38 kD protein on Western blots using homogenates of BDV-infected rat brain (S. Herzog, unpublished observations). To determine if antibodies in these human sera would recognize the 24 kD protein encoded by the B8 clone, $^{35}S$ labeled protein translated in vitro (as described above) was analyzed by immunoprecipitation. Antibodies in three out of seven of the patients' sera recognized the 24 kD protein (FIG. 5), including the serum previously shown by Western blot to recognize the 24 kD protein. It has been observed by Western blot analysis of human sera that either the 24 kD or the 38/39 kD protein is recognized but not both which is characteristic of immune serum from animals infected with BDV. However, no antibodies to the BDV protein were detected in seven normal controls.

These results suggest that a BDV-related virus is involved in behavioral disease in humans. Further, this cross reactivity will allow the use of cloned BDV proteins and nucleic acid to identify and isolate a BDV-related human virus.

The B8 cDNA clone characterized in this report represents a highly specific nucleic acid probe for the BDV agent. The clone most likely represents a cDNA copy of the 0.85 kb mRNA species. The fact that this clone strongly hybridizes to two other small mRNAs (3.6 and 2.1 kb) suggests that these mRNAs share common sequences. They could represent a nested set of partially overlapping mRNAs or mRNAs with common 5' leader or 3' specific sequences. The antigenic cross reaction between the 38/39 and 24 kD proteins suggests that the coding regions for the proteins overlap. The positive and negative strand probes hybridize with equal intensity to a 10.5 kb RNA species in BDV-infected rat brain RNA, strongly suggesting that the 10.5 kb RNA represents the viral genome.

The biology of the BDV agent resembles rabies virus in that both viruses are extremely neurotropic (Carbone, Virol. 61:3431 (1987)). Lymphocytic choriomeningitis virus (LCM) and BDV have similar immunopathological mechanisms which contribute to disease (Richt, J. Exp. Med. 170:1045 (1989)). Both rabies virus and LCM viruses have negative strand RNA genomes. However, the production of small cross-hybridizing mRNAs by the BDV agent is similar to the organization and gene expression observed for coronaviruses (Holmes, in: Virology, 2nd Ed., eds. Fields and Knipe, vol 1, pp. 841–856 (1990)). Thus, the isolation of cDNAs for the other BDV mRNAs and the genomic BDV RNA will be required to resolve the question of the genetic organization of the BDV. The molecular clone described in this report will allow further studies on the pathogenesis of Borna disease and allow the extension of such studies to human disease. The BDV agent appears to represent a new family or subfamily of viruses containing a unique genetic organization with highly neurovirulent biological properties and the ability to cause behavioral disease.

According to the present invention, DNA molecules are provided which are complementary to the Borna Disease Virus genome or the messenger RNA (mRNA) transcribed from viral sequences. Complementary sequences can be determined by inspection of sequences, adenine being complementary to uracil or thymine, and cytosine being complementary to guanine. Alternatively, complementarity can be determined by hybridization; single stranded sequences which are complementary hybridize to form duplex molecules under stringent hybridization conditions, as are known in the art.

Although applicants do not wish to be bound by any particular theory, it is believed that the BDV genome comprises RNA which is positive in polarity. That is to say, the genome is of the same polarity as the mRNA species. The genome is presumably transcribed into an intermediate of opposite polarity (negative) which is then transcribed into messages which are translated into proteins. The negative strand observed may also be a replicative intermediate. Alternatively, the genome itself may be a double stranded RNA molecule.

Antibodies for immunoprecipitation of BDV proteins can be polyclonal or monoclonal. Both are known in the art. (See for example, Haas, J. gen. Virol. 67:235 (1986). They can be raised against mixtures of viral proteins or purified proteins. They can be raised against synthetic peptides or fusion proteins containing BDV epitopes, as are disclosed herein.

The preparations of BDV proteins according to the present invention, are substantially free of mammalian proteins. They can be synthesized in vitro using techniques of synthetic chemistry, or translated using non-mammalian cell-free translation systems. Alternatively, they can be produced in recombinant organisms, such as *E. coli* carrying cloned BDV genes. The proteins can be fused to other non-BDV proteins, such as the bacterial β-galactosidase, as taught above.

Preparations which are substantially free of mammalian proteins comprise at least about 50% non-mammalian proteins and preferably greater than about 75% non-mammalian protein. More preferred are preparations which have less than about 10% or lell than about 5% mammalian proteins. Preparations which are substantially free of mammalian proteins do not demonstrate reactivity with rat or rabbit antisera in immunoblots to proteins other than the 38/39 kD, the 24 kD, the 15.5 kD, the 14.5 kD, and the 13 kD which are encoded by Borna Disease Virus. Due to the methods of producing the proteins which are provided herein, the proteins can be essentially free of mammalian proteins, i.e., containing less than about 0.05% mammalian proteins.

It is a finding of the present invention that mammalian cell cultures which have been infected with human cerebrospinal fluid (CSF) of patients having behavioral diseases elaborate RNA species which are similar to, but different from, Borna Disease Virus-encoded RNA. The human CSF-infected cells express RNA species which are of different sizes than those of BDV-infected cells. Furthermore the intensity of the hybridization signal of the RNA species expressed by the human CSF-infected cells is weaker than that of BDV-infected cells, when hybridization is to BDV-specific nucleotide probes. These results demonstrate that some humans having behavioral diseases, such as schizophrenia and bipolar depression, are infected with a BDV-related human virus. The ability of BDV to cause behavioral diseases in animals, suggests that the BDV-related human virus plays an etiological role in the human psychiatric disorders.

The cross-hybridization of the BDV-specific nucleotide probes with the nucleic acids from the human CSF-infected cell lines, and the cross-reactivity of human antisera with persistently BDV-infected cells (Rott, Science 228:755 (1985)) demonstrates that the BDV-specific proteins and nucleic acids taught herein, as well as BDV-specific antibodies can be used to isolate the BDV-related human virus. Furthermore, the results disclosed here demonstrate that the BDV-specific proteins and nucleic acids can be used diagnostically in humans as well as in other mammals.

In order to isolate the BDV-related human virus specific cDNA, the methods taught for isolation of BDV-specific cDNA are followed. However, instead of constructing the cDNA library from mRNA isolated from BDV-infected MDCK cell lines, the cDNA library is constructed from human CSF-infected cell lines, the human CSF coming from patients with behavioral disorders. Preferably the human CSF donors are pre-screened for serum immunofluorescence, as taught by Rott. The clones are selected either with BDV-specific antibodies or with BDV-specific DNA probes, as provided herein.

Immunological detection of BDV and BDV-related infections can be carried out according to any techniques known in the art. These may involve radioimmunoassay, ELISA, Western blots, radioimmunoprecipitation assays, etc. The particular techniques are practiced as are known in the art. Use of the substantially purified preparations of BDV-encoded proteins permits specific determination of the presence of a BDV or BDV-related human virus infection.

Kits are provided by the present invention for carrying out immunologcial detection of BDV and BDV-related human virus. The kits comprise a solid support with a preparation of Borna Disease Virus-encoded protein bound to the solid support. The solid support may include polystyrene or other plastic substance to which proteins are readily bound. The solid support can be in the form of a microtiter dish for performing ELISA assays, or a dipstick for performing a sandwich-type assay. Alternatively the solid support can be a matrix material for packing a column, such as is used in immunoaffinity chromatography. Other reagents for carrying out the assay may also be present in the kit, such as enzymes and chromogenic substrates to facilitate the detection of antibody-antigen complexes. The kits may contain one or more of the purified BDV-encoded proteins.

Methods for determining the presence of a BDV or BDV-related human virus are also contemplated as within the scope of the invention which utilize nucleic acid hybridization techniques. These can be done as is known in the art. Hybridizations can be performed on electrophoretically separated RNA species isolated from cells, as in the Northern technique. Alternatively, hybridizations can be performed in situ on fixed cells. Other assay techniques which are known can be used employing as specific probes the BDV-specific and BDV-related human virus-specific nucleic acids provided herein.

```
                                  SEQ ID NO: 1

DNA sequence 707 b.p. ATAAAAAACCAA ... AAAAAAAAAAAA linear

|    10    |    20    |    30    |    40    |    50    |    60
         1  ATAAAAAACC AAATGCGGCA AACCCCCCGC GACCTGTGAT GAGTTCCGAC CTCCGGCTGA  60
        61  CATTGCTTGA ATTAGTCAGG AGGCTCAATG GCAACGCGAC CATCGAGTCT GGTCGACTCC 120
       121  CTGGAGGACG AAGAAGATCC CCAGACACTA CGACGGGAAC GGTCGGCGTC ACCAAGACCA 180
       181  CGGAAGATCC CAAGGAATGC ATTGACCCAA CCGGTAGACC AGCTCCTGAA GGACCTCAGG 240
       241  AAGAACCCCT CCATGATCTC AGACCCAGAC CAGCGAACCC GAAGGAGCAG CTATCGAATG 300
       301  ATGAGCTTAT CAAGAAGCTA GTGACGGAGC TGGCCGAGAA TAGCATGATC GAGGCTGAGG 360
       361  AGGTGCGGGG CACTCTTGGG GACATCTCGG CTCGCATCGA GGCAGGGTTT GAGTCCCTGT 420
       421  CCGCCCTCCA AGTGGAAACC ATCCAGACAC TCAGCGGTGC GACCACTCCG ATAGCATCAG 480
       481  AATTCCTTGG CGAGAACATC AAGATACTGG ATCGCTCCAT GAAGACAATC ATGGAGACAA 540
       541  TGAAGCTCAT GATGGAGAAG GTGGACCTCC TCTACGCATC AACCGCCGTT GGGACCTCTG 600
       601  CACCCATGTT GCCCTCCCAT CCTGCACCTC CGCGCATTTA TCCCCAGCTC CCAAGTGCCC 660
       661 CGACAGCGGA TGAGTGGGAC ATCATACCAT  AAAAAAAAAA AAAAAAA               707
              |    10    |    20    |    30    |    40    |    50    |    60
```

What is claimed is:

1. A method of determining a Borna Disease Virus infection in animals or a Borna Disease Virus-related human virus infection in humans, comprising the steps of:

providing a serum sample of an animal or human to be tested;

contacting the serum sample with a preparation of Borna Disease Virus-encoded protein substantially free of mammalian proteins, under conditions where antibody-antigen complexes form and are stable;

determining the presense of antibody-antigen complexes which contain said Borna Disease Virus-encoded protein, the presense of antibody-antigen complexes which contain said Borna Disease Virus-encoded protein indicating a Borna Disease Virus infection or a Borna Disease Virus-related human virus infection.

2. The method of claim 1 wherein said Borna Disease Virus-encoded protein is selected from the group consisting of: an approximately 24 kD protein, an approximately 15.5 kD protein, an approximately 14.5 kD protein and an approximately 13 kD protein.

3. The method of claim 1 wherein the preparation comprises an approximately 24 kD protein, an approximately 15.5 kD protein, an approximately 14.5 kD protein and an approximately 13 kD protein.

4. A method determining a Borna Disease Virus infection in animals or a Borna Disease Virus-related human virus infection in humans, comprising the steps of:

providing a sample of cells from an animal or human to be tested;

extracting RNA from said cells;

contacting said RNA with a DNA probe, said probe comprising a DNA molecule which is complementary to a Borna Disease Virus-encoded messenger RNA;

determining the presence of hybrid molecules comprising said probe, the presence of said hybrid molecules indicating a Borna Disease Virus infection or a Borna Disease Virus-related human virus infection.

5. A method of determining a Borna Disease Virus infection in animals or a Borna Disease Virus-related human virus infection in humans, comprising the steps of:

providing a sample of cells from an animal or human to be tested;

permeabilizing said cells;

contacting said permeabilized cells with a DNA probe, said probe comprising a DNA molecule which is complementary to a Borna Disease Virus-encoded messenger RNA;

determining the presence of hybrid molecules comprising said probe, the presence of said hybrid molecules indicating a Borna Disease Virus infection or a Borna Disease Virus-related human virus infection.

6. A method of determining a Borna Disease Virus-related human virus infection in humans, comprising the steps of:

providing a sample of cells from a human to be tested;

extracting RNA from said cells;

contacting said RNA with a DNA probe, said probe comprising a DNA molecule which is complementary to a Borna Disease Virus-related human virus-encoded messenger RNA;

determining the presence of hybrid molecules comprising said probe, the presence of said hybrid molecules indicating a Borna Disease Virus-related human virus infection.

7. A method of determining a Borna Disease Virus-related human virus infection in humans, comprising the steps of:

providing a sample of cells from a human to be tested;

permeabilizing said cells;

contacting said permeabilized cells with a DNA probe, said probe comprising a DNA molecule which is complementary to a Borna Disease Virus-related human virus-encoded messenger RNA;

determining the presence of hybrid molecules comprising said probe, the presence of said hybrid molecules indicating a Borna Disease Virus-related human virus infection.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 707 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO -continued

```
    (vi) ORIGINAL SOURCE:
         (A) ORGANISM: Borna Disease Virus (vii) IMMEDIATE SOURCE:
         (B) CLONE: B8

(xi) SEQUENCE DESCRIPTION: SEQ ID NO:1:

ATAAAAAACC AAATGCGGCA AACCCCCCGC GACCTGTGAT GAGTTCCGAC CTCCGGCTGA      60

CATTGCTTGA ATTAGTCAGG AGGCTCAATG GCAACGCGAC CATCGAGTCT GGTCGACTCC     120

CTGGAGGACG AAGAAGATCC CCAGACACTA CGACGGGAAC GGTCGGGGTC ACCAAGACCA     180

CGGAAGATCC CAAGGAATGC ATTGACCCAA CCGGTAGACC AGCTCCTGAA GGACCTCAGG     240

AAGAACCCCT CCATGATCTC AGACCCAGAC CAGCGAACCG GAAGGAGCAG CTATCGAATG     300

ATGAGCTTAT CAAGAAGCTA GTGACGGAGC TGGCCGAGAA TAGCATGATC GAGGCTGAGG     360

AGGTGCGGGG CACTCTTGGG GACATCTCGG CTCGCATCGA GGCAGGGTTT GAGTCCCTGT     420

CCGCCCTCCA AGTGGAAACC ATCCAGACAC TCAGCGGTGC GACCACTCCG ATAGCATCAG     480

AATTCCTTGG CGAGAACATC AAGATACTGG ATCGCTCCAT GAAGACAATG ATGGAGACAA     540

TGAAGCTCAT GATGGAGAAG GTGGACCTCC TCTACGCATC AACCGCCGTT GGGACCTCTG     600

CACCCATGTT GCCCTCCCAT CCTGCACCTC CGCGCATTTA TCCCCAGCTC CCAAGTGCCC     660

CGACAGCGGA TGAGTGGGAC ATCATACCAT AAAAAAAAAA AAAAAAA                   707
```